(12) United States Patent
Piantoni et al.

(10) Patent No.: US 10,470,940 B2
(45) Date of Patent: Nov. 12, 2019

(54) DEVICE FOR FORMING AND APPLYING AT LEAST ONE PAIR OF ACCESSORY ELEMENTS ON A CONTINUOUS BAND OF ABSORBENT MATERIAL AND MACHINE FOR MAKING ABSORBENT SANITARY ARTICLES COMPRISING THE DEVICE

(71) Applicant: GDM S.p.A., Bologna (IT)

(72) Inventors: Matteo Piantoni, Albino (IT); Valerio Soli, Bologna (IT)

(73) Assignee: GDM S.P.A., Bologna (IT)

(*) Notice: Subject to any disclaimer, the term of this patent is extended or adjusted under 35 U.S.C. 154(b) by 359 days.

(21) Appl. No.: 15/504,929

(22) PCT Filed: Aug. 4, 2015

(86) PCT No.: PCT/IB2015/055910
§ 371 (c)(1),
(2) Date: Feb. 17, 2017

(87) PCT Pub. No.: WO2016/030783
PCT Pub. Date: Mar. 3, 2016

(65) Prior Publication Data
US 2017/0252223 A1  Sep. 7, 2017

(30) Foreign Application Priority Data
Aug. 27, 2014  (IT) .............................. BO2014A0466

(51) Int. Cl.
*A61F 13/15* (2006.01)
*H02K 41/03* (2006.01)
*H02P 8/00* (2006.01)

(52) U.S. Cl.
CPC .. *A61F 13/15756* (2013.01); *A61F 13/15723* (2013.01); *A61F 13/15764* (2013.01);
(Continued)

(58) Field of Classification Search
CPC .......... A61F 13/15577; A61F 13/15585; A61F 13/15756; A61F 13/15723;
(Continued)

(56) References Cited

U.S. PATENT DOCUMENTS 6,730,189 B1 * 5/2004 Franzmann ....... A61F 13/15756
156/265
9,968,491 B2 * 5/2018 Piantoni ............ A61F 13/15756
(Continued)

FOREIGN PATENT DOCUMENTS

CN          1808863 A      7/2006
CN        101257874 A      9/2008
(Continued)

OTHER PUBLICATIONS

International Search Report and Written Opinion dated Sep. 21, 2015 from counterpart PCT App No. PCT/IB2015/055910.
(Continued)

*Primary Examiner* — Alexander M Valvis
*Assistant Examiner* — Himchan "Aiden" Song
(74) *Attorney, Agent, or Firm* — Shuttleworth & Ingersoll, PLC; Timothy J. Klima

(57) ABSTRACT

A device for forming and applying accessory elements to a continuous band of absorbent material, includes a unit for feeding a continuous strip to a conveyor roller, a unit for cutting the strip in a continuous and alternating succession of first and second pieces, a first and a second roller rotating about respective axes parallel to the first direction, each including a movement device acting along a circumferential direction around the respective axis and configured for imparting to each unit a respective motion between positions for picking up and releasing the pieces. A unit for applying a pair of pieces to the band is equipped with a separating unit equipped with a spacer device for moving first and/or second
(Continued)

carriages along a separating direction between close and far axial positions, wherein the spacer device includes a plurality of linear actuators each associated with a respective first carriage.

12 Claims, 11 Drawing Sheets

(52) U.S. Cl.
CPC ..... *A61F 13/15804* (2013.01); *H02K 41/031* (2013.01); *H02P 8/005* (2013.01)

(58) Field of Classification Search
CPC .......... A61F 13/15764; A61F 13/15804; A61F 2013/15821; B32B 38/0004; B32B 37/0053; Y10T 156/1077; Y10T 156/1087; Y10T 156/1098; Y10T 156/1322; B31D 1/04; B31D 1/0081; B31D 1/00; H02K 41/031; H02P 8/005
USPC .......................... 493/344, 345, 346, 347, 394
See application file for complete search history.

(56) References Cited

U.S. PATENT DOCUMENTS

| | | | |
|---|---|---|---|
| 2002/0000291 A1* | 1/2002 | Coenen | A41H 37/00 156/267 |
| 2006/0168745 A1 | 8/2006 | Kobayashi et al. | |
| 2008/0276439 A1* | 11/2008 | Andrews | A61F 13/15577 29/428 |
| 2009/0321986 A1 | 12/2009 | Perego et al. | |
| 2010/0192739 A1 | 8/2010 | Piantoni et al. | |
| 2010/0326796 A1* | 12/2010 | Walsh | A61F 13/15764 198/579 |
| 2012/0100978 A1 | 4/2012 | Tommasi | |
| 2012/0190523 A1 | 7/2012 | Pastrello et al. | |
| 2013/0035222 A1* | 2/2013 | Andrews | A61F 13/15723 493/342 |
| 2015/0024919 A1* | 1/2015 | Shimada | A61F 13/49 493/344 |
| 2016/0354257 A1* | 12/2016 | Csida | A61F 13/15756 |
| 2017/0233188 A1* | 8/2017 | Tai | B65G 1/0457 414/281 |

FOREIGN PATENT DOCUMENTS

| | | |
|---|---|---|
| CN | 102482043 A | 5/2012 |
| EP | 1303240 A2 | 4/2003 |
| JP | 2004504107 A | 2/2004 |
| WO | WO200207664 A2 | 1/2002 |
| WO | 2013035067 A1 | 3/2013 |
| WO | WO2014087293 A1 | 6/2014 |

OTHER PUBLICATIONS

Chinese Office Action dated Apr. 16, 2019 for counterpart Chinese Patent Application No. 201580045788.0.
Japanese Office Action dated May 31, 2019 for counterpart Japanese Patent Application No. JP2017511212 0.

* cited by examiner

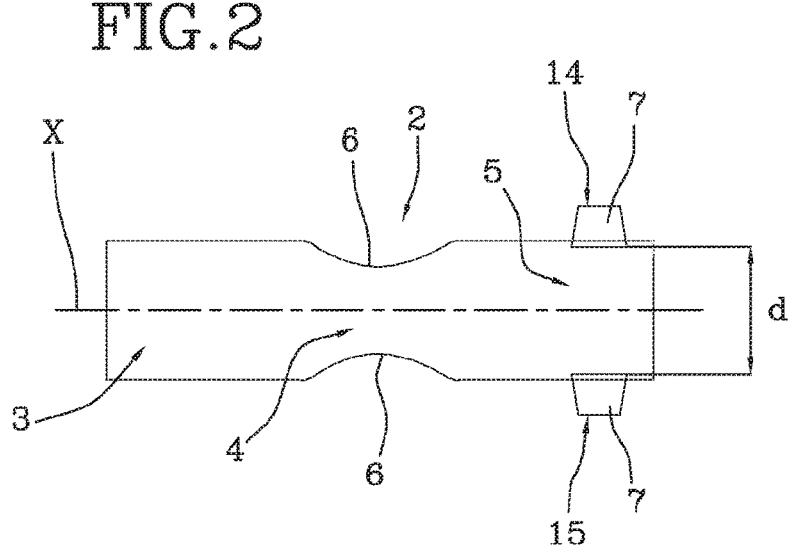
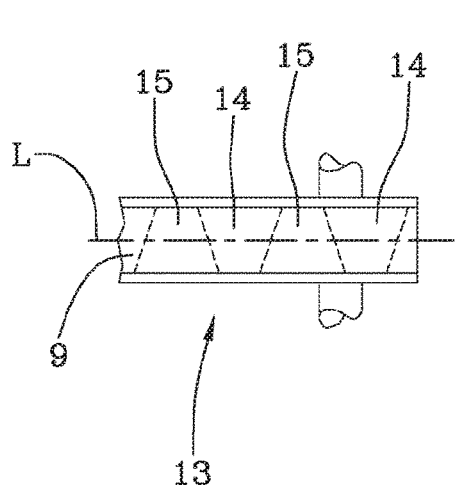
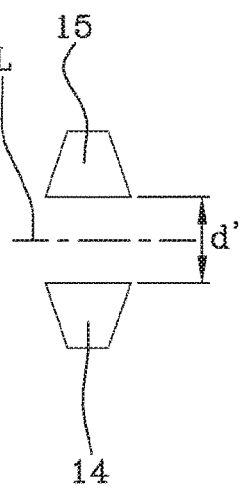
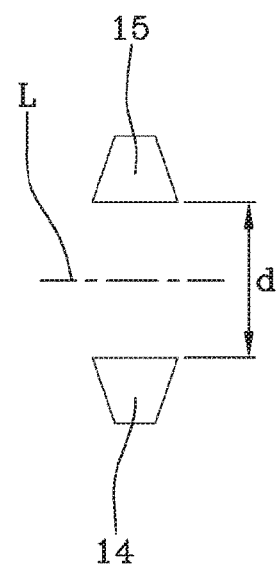

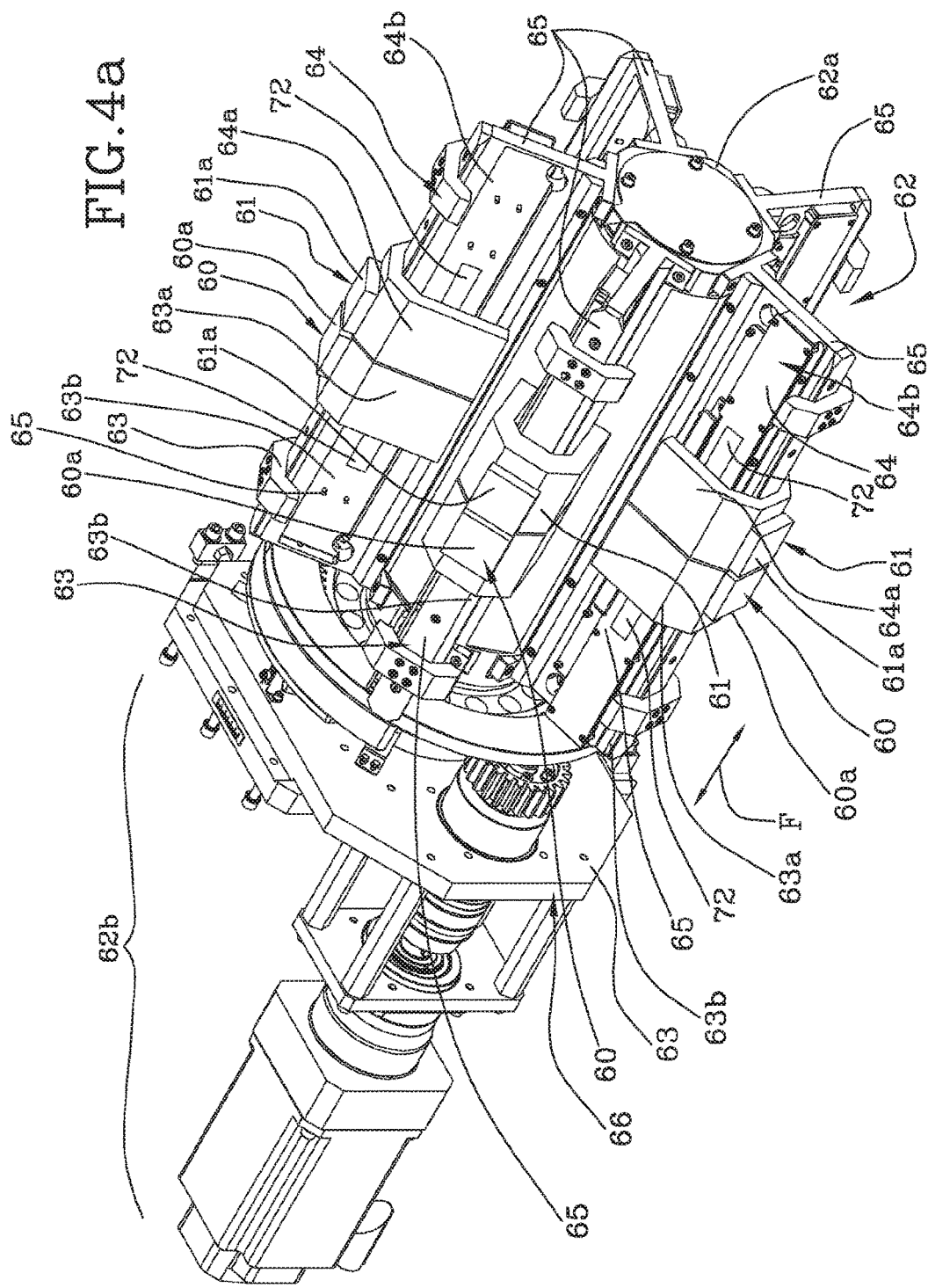

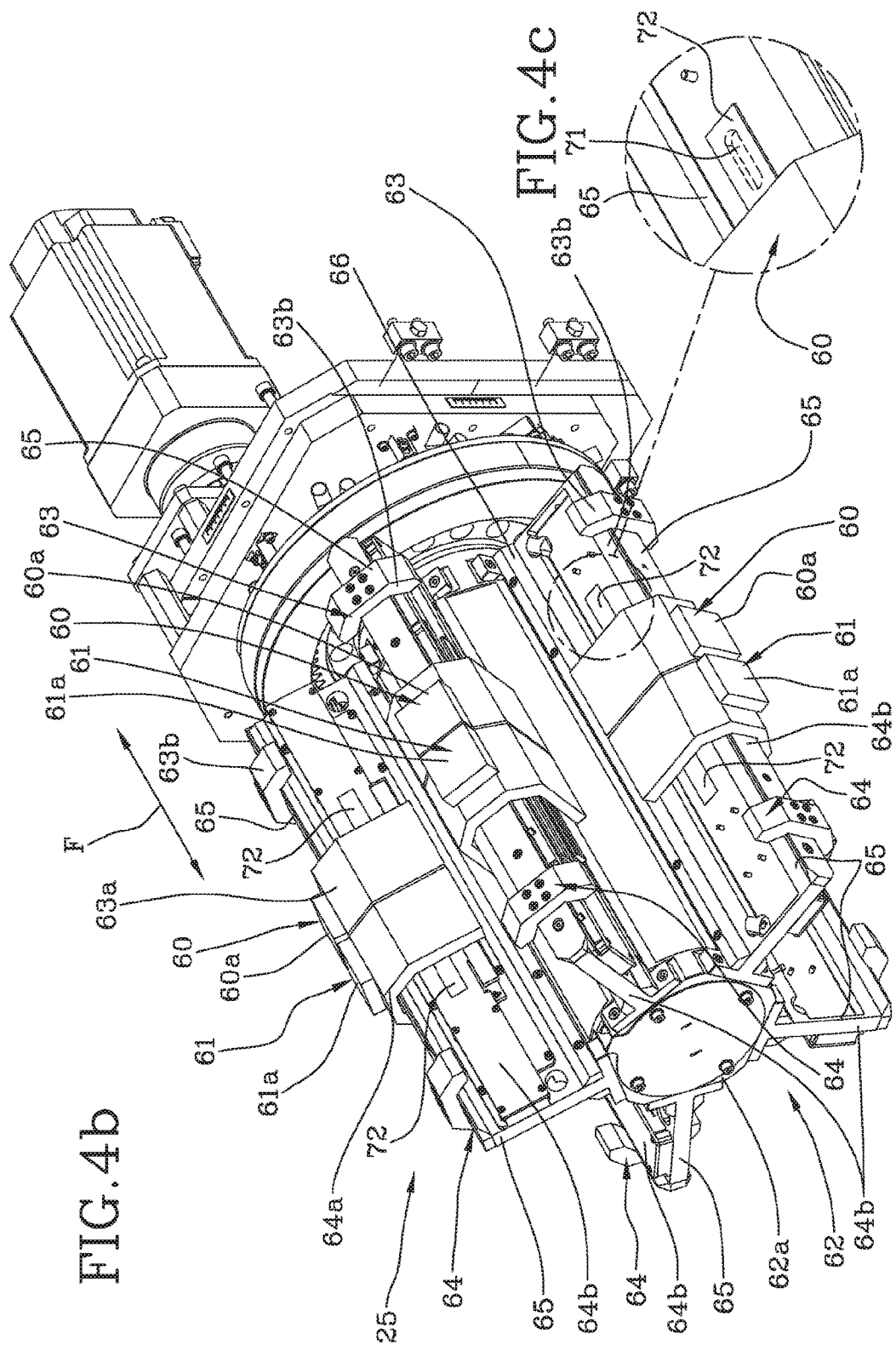

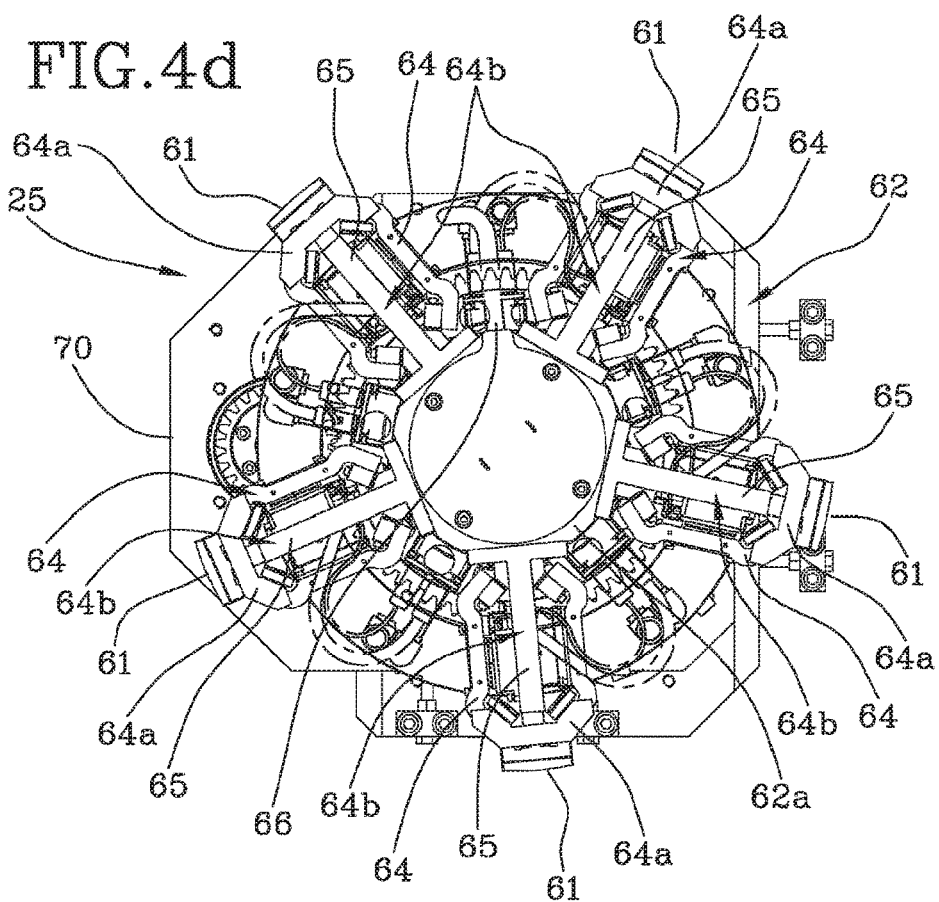
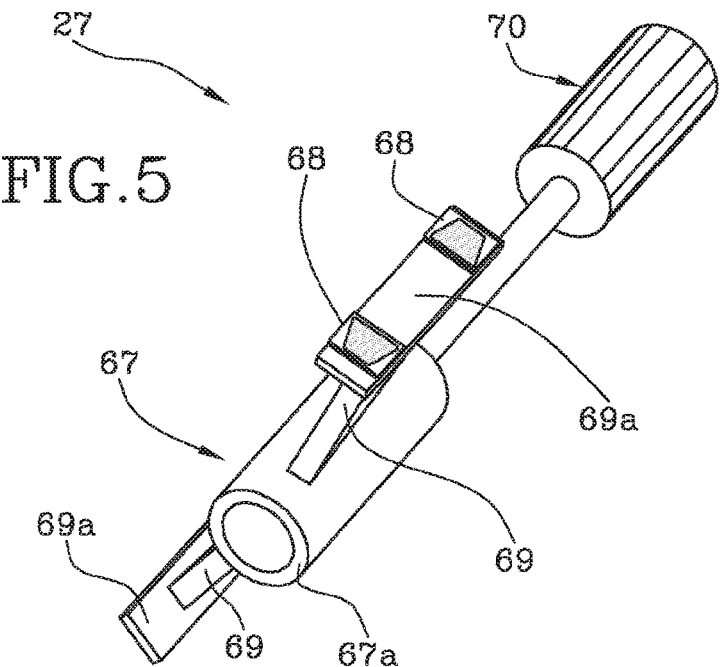

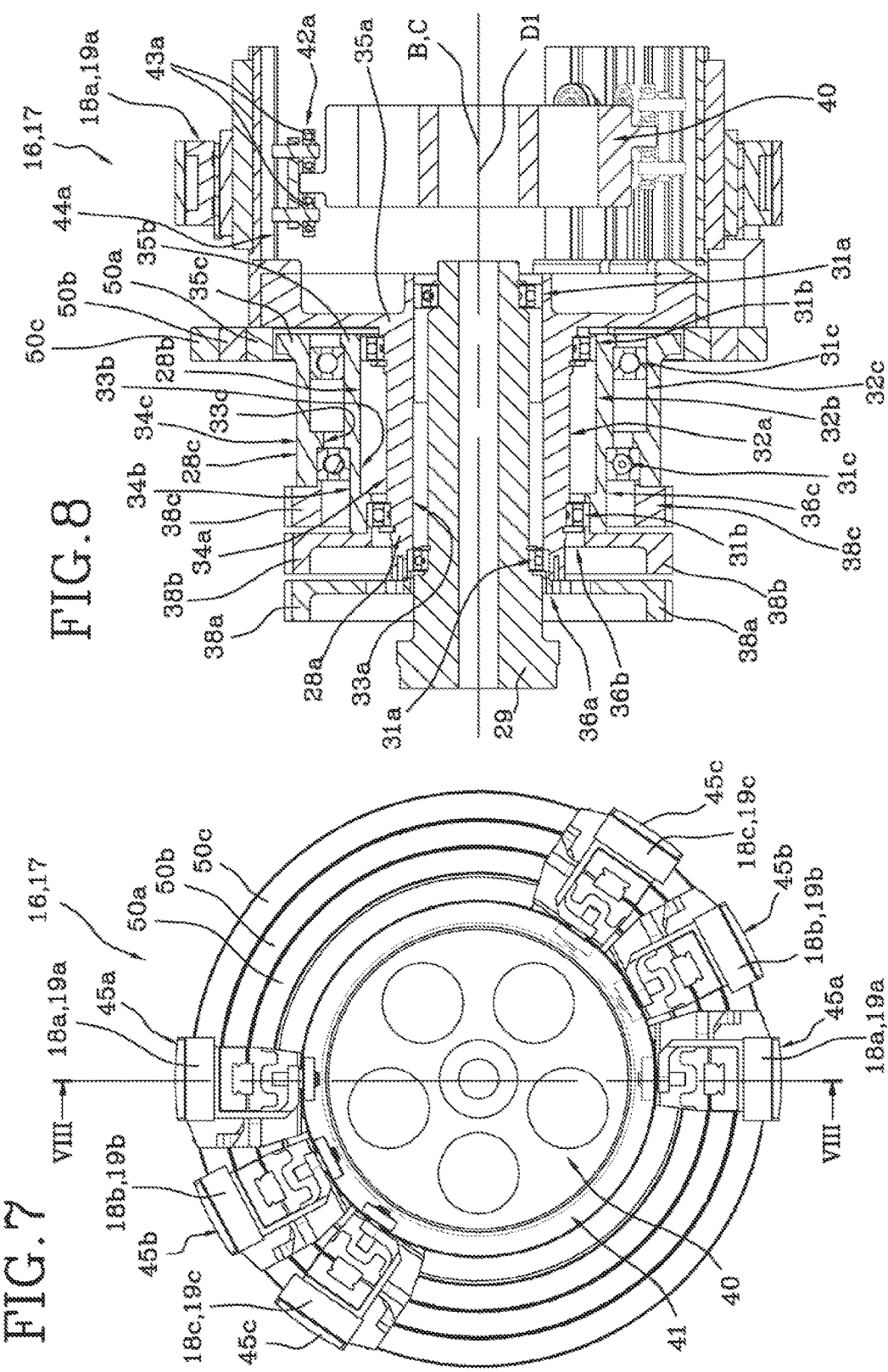

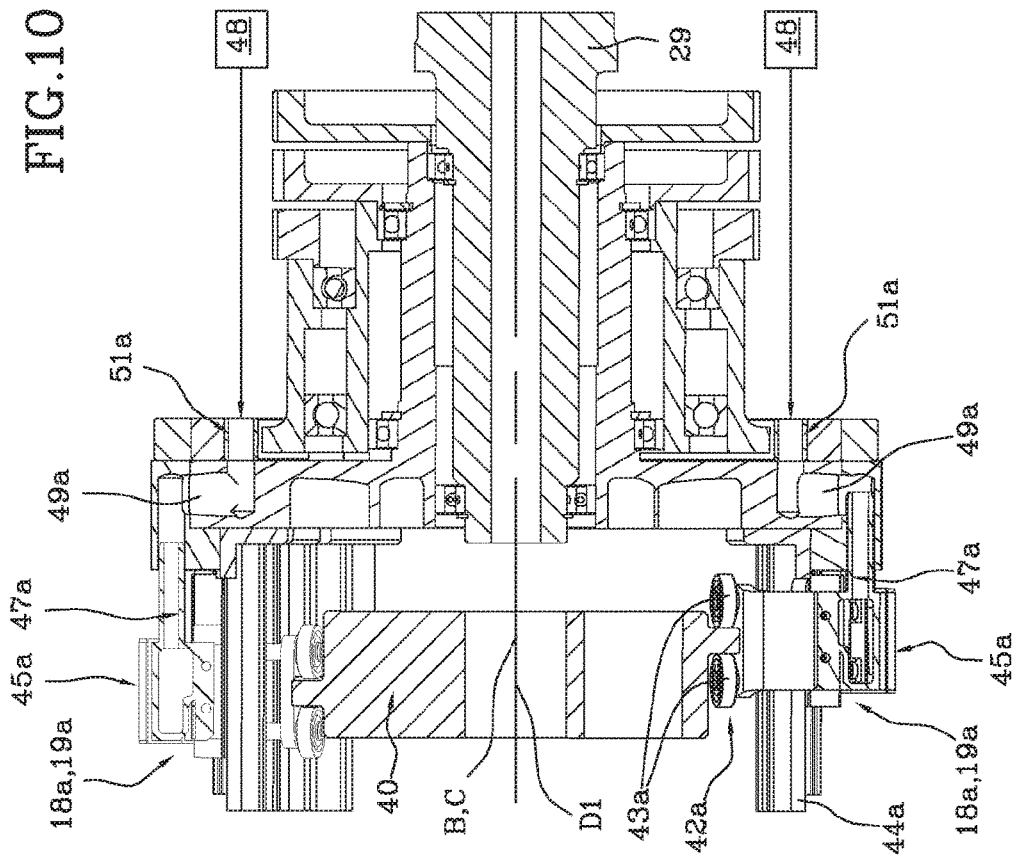
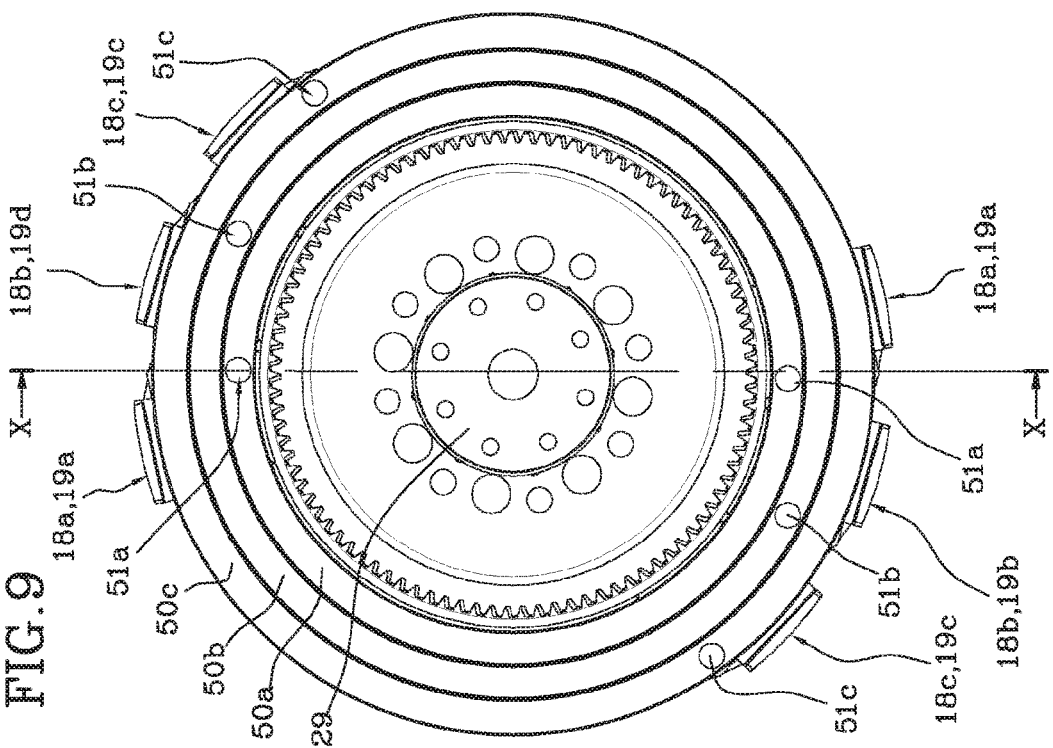

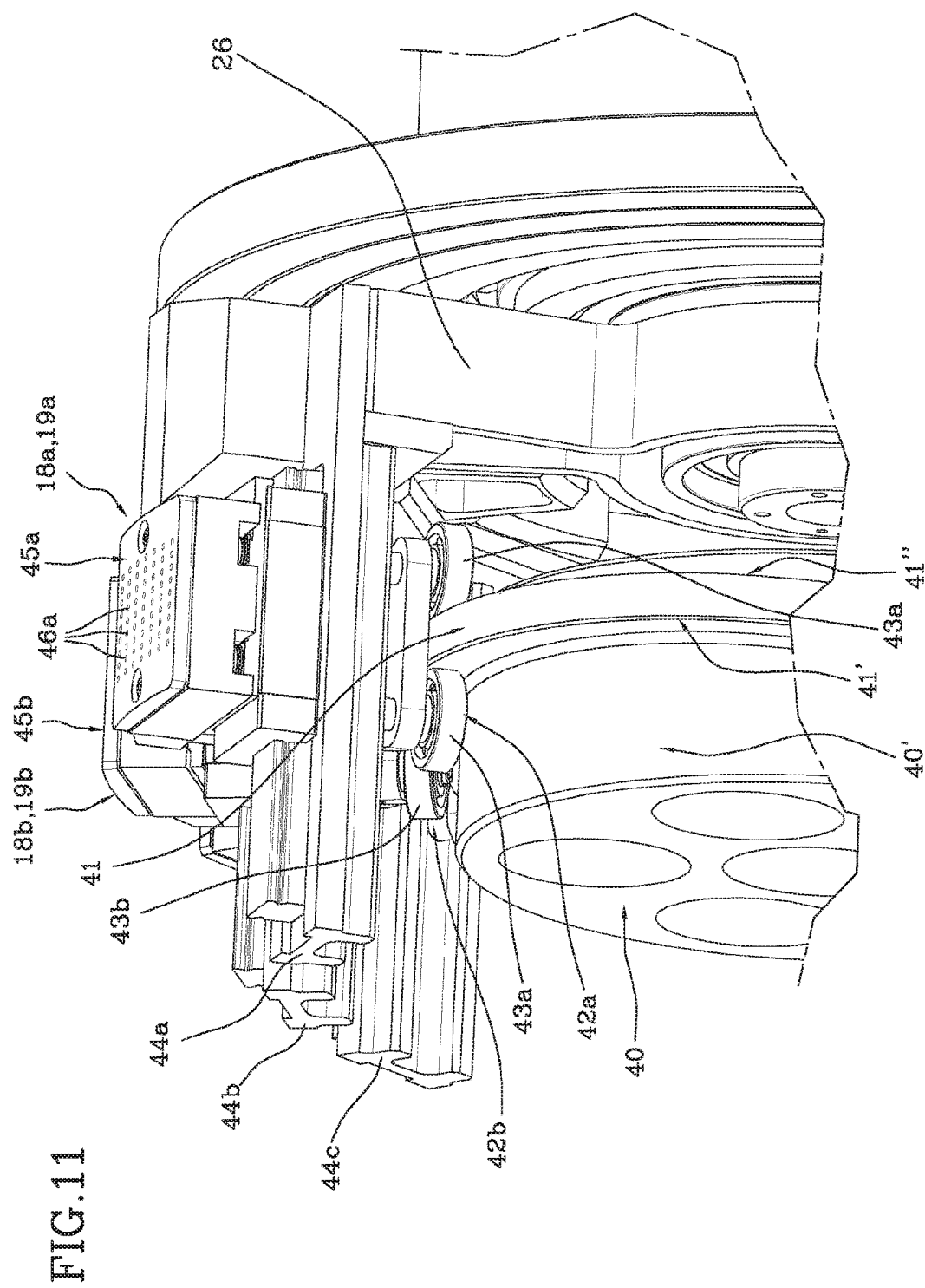

DEVICE FOR FORMING AND APPLYING AT LEAST ONE PAIR OF ACCESSORY ELEMENTS ON A CONTINUOUS BAND OF ABSORBENT MATERIAL AND MACHINE FOR MAKING ABSORBENT SANITARY ARTICLES COMPRISING THE DEVICE

This application is the National Phase of International Application PCT/IB2015/055910 filed Aug. 4, 2015 which designated the U.S.

This application claims priority to Italian Patent Application No. BO2014A000466 filed Aug. 27, 2014, which application is incorporated by reference herein.

TECHNICAL FIELD

This invention relates to a device for forming and applying at least one pair of accessory elements on a continuous band of absorbent material and a machine for making absorbent sanitary articles comprising the device.

BACKGROUND ART

More specifically, the invention relates to a device which can be inserted in a machine for making absorbent sanitary articles such as disposable nappies for children or adults.

As is known, these articles are obtained by laying a sheet of impermeable material over a sheet of permeable material (of non-woven fabric), with a padding consisting of an absorbent pad interposed between the two sheets. More specifically, both in the case of nappies of children and in the case of nappies for adults, it is usual to add accessory components such as lateral flaps for closing the nappy round the wearer's waist.

Generally speaking, in the prior art machines, the lateral closure flaps are applied along certain stretches of a continuous web of a material for making nappies, these stretches corresponding to the single nappies, when subsequently divided.

These machines comprise a conveyor for feeding a continuous strip of elastomeric material, a unit for cutting a continuous strip of elastomeric material into suitably shaped single pieces constituting the lateral flaps for closing the nappies, and a unit for applying pairs of lateral flaps to the continuous band.

The cutting unit makes a succession of pieces forming the above-mentioned lateral flaps which are fed by a conveyor roller to the unit for applying the pairs of lateral flaps.

More in detail, each pair of lateral flaps is defined by a first and a second piece, and the cutting unit makes a continuous and alternating succession of first and second pieces.

Between the conveyor roller and the application unit, the machine has a pair of spacer rollers, which are able to pick up respective pieces from the continuous succession fed by the conveyor roller.

A first spacer roller picks up from the succession only the first pieces, whilst the second picks up only the second pieces.

The first and the second roller feed the respective pieces to the application unit, which makes the respective pairs of first and second pieces, which are mutually aligned and spaced by a predetermined length on the basis of the transversal dimensions of the continuous band of a material for making nappies. The application unit then applies in step each pair on the continuous band.

A solution of this kind, for example, is known from patent publication WO2014/087293 in the name of the same Applicant as this invention.

More specifically, the solution shown in that document describes a device in which the application unit is defined by a spacer roller configured to move the two pieces of material of the pair of accessory elements away from each other, so as to bring them to an operating distance for applying the band of absorbent material.

More specifically, the patent document WO2014/087293 specifies that the axial movement of the two pieces along the spacer roller is obtained by mechanical means, such as, for example, gears, gear wheels or cams, connected to the means for rotating the roller, or transfer rollers, so as to link the movements to each other.

However, it is known how, with the variation in the type of absorbent article to be made, the dimensions and the format of the lateral flaps also vary.

It follows that the distance between the two pieces of the single pair must vary as a function of the size of the article, thus resulting in a resetting of the entire kinematic mechanism for moving and transferring the accessory elements.

In effect, since they are connected to each other by mechanical transmission means, it follows that the rotation speed of the roller is linked to the distance of separation between the tabs, and the feed speed of the various components is also linked.

Consequently, the prior art machines, even though they have high levels of performance and production rates, have major drawbacks linked to the maintenance and setup times during size change-overs.

DISCLOSURE OF THE INVENTION

The aim of this invention is to provided a device for forming and applying at least one pair of accessory elements on a continuous band of absorbent material and a machine for making absorbent sanitary articles which overcome the above-mentioned drawbacks of the prior art.

More specifically, the main aim of this invention is to provide a device for forming and applying at least one pair of accessory elements on a continuous band of absorbent material which is extremely versatile and flexible in the management of products having different sizes.

A further aim of this invention is to provide a machine for making absorbent sanitary articles wherein it is simple to set up size changes.

Yet another aim of this invention is to provide a device for forming and applying at least one pair of accessory elements on a continuous band of absorbent material which is easy to control and easy to install in an existing machine for making absorbent sanitary articles.

The aims are fully achieved by a device for forming and applying at least one pair of accessory elements on a continuous band of absorbent material comprising the technical features described in one or more of the appended claims and, more specifically, by a device for forming and applying at least one pair of accessory elements on a continuous band of absorbent material, comprising a unit for feeding a continuous strip to a conveyor roller, which rotates about an axis transversal to a first reference direction and a unit for cutting the strip in a continuous and alternating succession of first and second pieces, constituting, respectively, first and second accessory elements of the absorbent article.

The device also comprises a first and a second roller rotating about respective axes parallel to the first path and each equipped with a plurality of units for picking up, respectively, first and second pieces, from the succession and releasing them at a release position, wherein each transfer roller comprises means for moving the units acting along a circumferential direction around the respective axis and configured for imparting to each unit a respective law of motion between a position for picking up the pieces located on the conveyor roller, and the position for releasing the pieces, means for translating the units acting along a direction parallel to the first direction and configured for moving each unit between a first axial position, adopted in the picking up position, and a second axial position, adopted in the release position.

The device is also equipped with a unit for applying a pair of pieces to the band of absorbent material positioned operatively downstream of the rollers and equipped with a separating unit configured for picking up the pieces from the release position of the first and the second roller by means of respective first and second carriages; the unit being equipped with spacer means configured for moving the first and/or second carriage along a separating direction, parallel to the first direction, between a close axial position, wherein each first carriage is aligned and located at a predetermined intermediate distance from a respective second carriage, and a far axial position wherein the carriages are located at an operating distance which is greater than the intermediate distance.

According to a main aspect of this invention, the spacer means comprise a plurality of linear actuators each associated with a respective first carriage.

Advantageously, in this way it is possible to separate the movement of the pieces away from each other from their feeding, thus allowing a greater its versatility of the device, and, consequently, of the system.

BRIEF DESCRIPTION OF DRAWINGS

These and other features of the invention will become more apparent from the following detailed description of a preferred, non-limiting embodiment of it, with reference to the accompanying drawings, in which:

FIG. 2 is a plan view of an absorbent sanitary article obtained from the machine of FIG. 1;

FIGS. 3a, 3b and 3c schematically illustrate several operational steps of the machine of FIG. 1;

FIGS. 4a, 4b are different perspective views of a first detail of the device of FIG. 1;

FIG. 4c is a detail of FIG. 4b;

FIG. 4d is a front view of the detail of FIGS. 4a, 4b;

FIG. 5 is a perspective view of a second detail of the device of FIG. 1;

FIG. 7 is a front view of the detail of FIG. 6;

FIG. 8 is a sectional view of the detail of FIG. 6 through the plane VIII-VIII of FIG. 7;

FIG. 9 is a rear view of the detail of FIG. 6;

FIG. 10 is a sectional view of the detail of FIG. 6 through the plane X-X of FIG. 9;

FIG. 11 is an enlarged perspective view of a fourth detail of the machine of FIG. 1;

DETAILED DESCRIPTION OF PREFERRED EMBODIMENTS OF THE INVENTION

Figure 1:
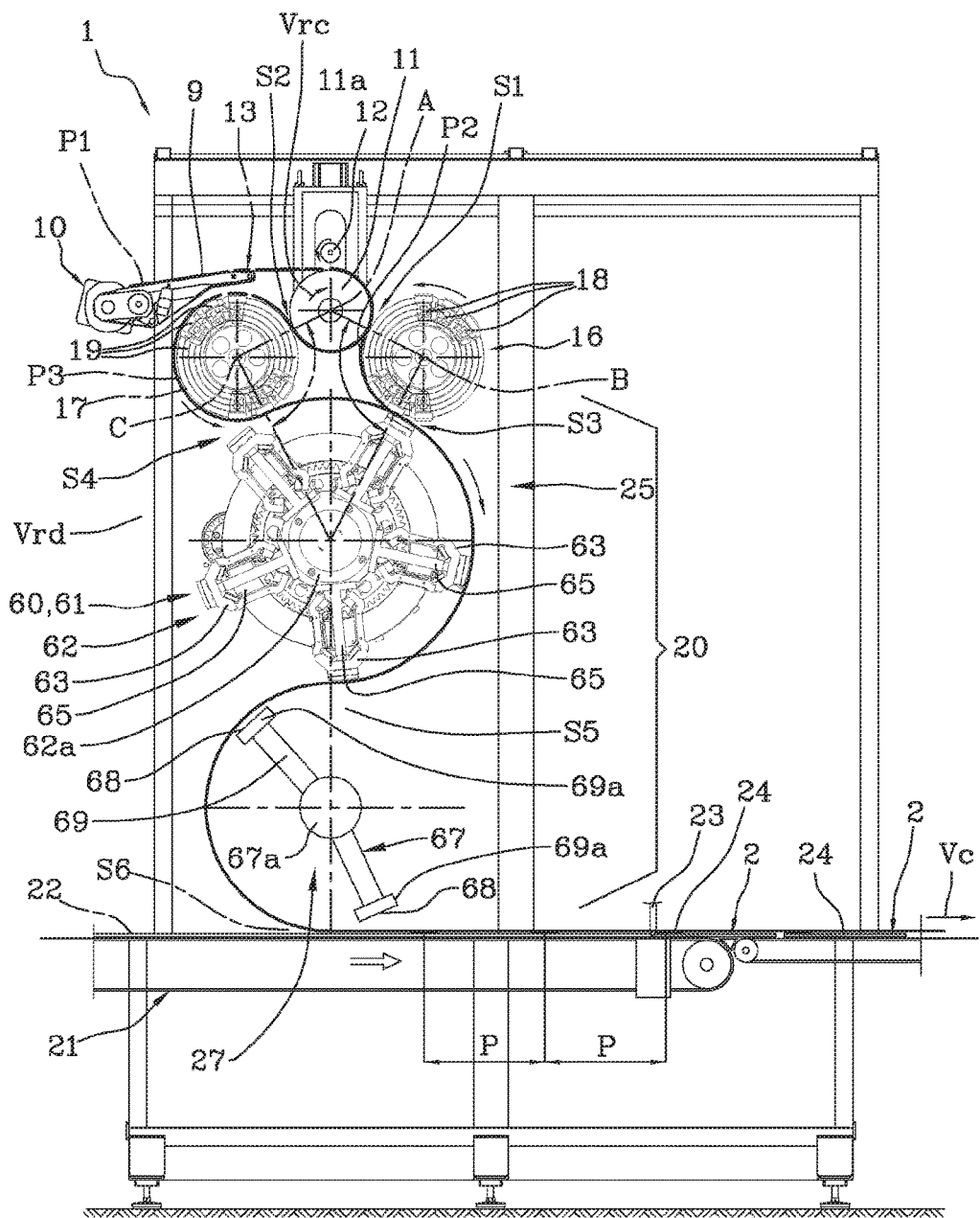
FIG. 1 is a front view of a machine for making absorbent sanitary articles equipped with a device according to this invention.

With reference to FIG. 1, the numeral 1 denotes in its entirety a device for forming and applying at least one pair of accessory elements on a continuous band of absorbent material, preferably installed in a machine for making absorbent sanitary articles 2 in accordance with this invention.

The absorbent article 2, as shown in detail in FIG. 2, is substantially rectangular in shape and extends along a longitudinal axis X.

The absorbent articles 2 comprise, in a line along the axis X, a front portion 3, a central portion 4 and a rear portion 5.

At the central portion 4, the absorbent articles 2 comprise a recess 6, or leg opening, formed by two arched stretches which are symmetrical relative to the axis X.

The absorbent articles 2 comprise an internal absorbent padding, normally made from cellulose fibres, placed inside a soft container defined on one side by a permeable sheet of non-woven fabric and, on the other side, by an impermeable sheet of polyethylene.

The absorbent article 2 is also equipped with a pair of accessory element, that is lateral flaps 7, extending transversely to the axis X. More specifically, the lateral flaps 7 extend from the rear portion 5 of the absorbent article 2 and are, in use, designed to be placed over respective fastening zones of the front portion 3 in order to close the absorbent article 2 round the wearer's hips.

The lateral flaps 7 generally comprise pieces of a continuous strip 9, defining a longitudinal axis L (FIG. 3a) and preferably made from elastomeric material. Moreover, the lateral flaps 7 have a surface which is partly covered with an adhesive substance, or provided with other quick fastening means.

It should be noted that the accessory elements 7 which, as mentioned above, define the lateral flaps of the absorbent article 2, and are denoted by the same reference numeral 7, therefore also consist of the above-mentioned pieces. In other words, in this specific case, the accessory elements and the lateral flaps coincide and both consist of the above-mentioned pieces.

The device 1 comprises a unit 10 for feeding the above-mentioned continuous strip 9 of elastomeric material to a conveyor roller 11, which rotates about an axis "A" transversal to a first reference direction "D1" of the device 1.

Moreover, the device 1 comprises a unit 12 for cutting the strip 9 into a continuous and alternating succession 13 of first 14 and second 15 pieces.

Thus, the conveyor roller 11 rotates about an axis A parallel to a first reference direction D1, defined by a direction perpendicular to the plane of FIG. 1, and has a relative sucked surface 11a for retaining the above-mentioned succession 13 of first 14 and second 15 pieces during their transfer.

The cutting unit 12 preferably comprises a cutting roller, rotating in an opposite direction to the conveyor roller 11, with which acts in conjunction in order to make the continuous succession 13 of first 14 and second 15 pieces. More in detail, the first pieces 14 are applied on one side of the article 2 having a first of the above-mentioned recesses 6, whilst the second pieces 15 are applied on the opposite side of the article 2 equipped with the second recess 6.

The cutting roller 12 is equipped, preferably, with a pair of blades which are skew to each other and inclined transversely to the axis of rotation of the roller 12 itself. The blades positioned in this way make cuts which are oblique relative to the longitudinal direction of the continuous succession 13, thus forming substantially trapezoidal pieces 14 and 15 (FIG. 3a).

The device 1 also comprises a first transfer roller 16, which rotates about a relative axis B parallel to the first direction D1 and it is equipped with a plurality of units 18 for retaining and transferring the first pieces 14, which are picked up by the sucked surface 11a of the conveyor roller 11 at a first pick-up station S1.

Similarly, the device 1 also comprises a second transfer roller 17, which rotates about a relative axis C parallel to the first direction D1 and it is equipped with a plurality of units 19 for retaining and transferring the second pieces 15, which are picked up by the sucked surface 11a of the conveyor roller 11 at a second pick-up station S2.

More specifically, it is preferable and advantageous that the first 16 and the second 17 transfer roller are equal, in such a way as to simplify the structure of the device 1, and thus of the machine on which it is mounted.

As further illustrated in FIG. 1, the device comprises a unit 20 for applying on a continuous band 22 of absorbent material at least a pair of pieces for each absorbent article 2. Each pair is formed by a first 14 and by a second 15 piece, which are mutually aligned and spaced by an operational distance "d" and aligned along the first direction D1.

It should be noted that, downstream of the application unit 20, the machine to which the device 1 is associated (and of which the device 1 forms part) comprises a conveyor 21 which is able to feed with a speed "vc" the continuous band 22 of absorbent material along a second direction D2, transversal (preferably at right angles) to the above-mentioned direction D1, and a unit 23 for cutting the continuous band 22 into pieces 24 of absorbent material designed to constitute single absorbent articles 2.

The application unit 20 applies the respective pairs of pieces 14 and 15 on the continuous band 22 spaced by a step P, measured along the direction D2. The step P coincides with the step according to which are cut the above-mentioned pieces 24 of absorbent material, designed to constitute the single absorbent articles 2. According to one aspect of this invention, the application unit 20 comprises a separating unit 25 configured to pick up the pieces 14, 15 from the release position of the first 16 and the second roller 17 by means of respective first 60 and second carriages 61.

Thus, the separating unit 25 is configured for receiving, at a third station S3, the first pieces 14 fed by the first transfer roller 16 and, at a fourth station S4, the second pieces 15 fed by the second transfer roller 17.

At these third and/or fourth stations S3, S4, the first 14 and the second pieces 15 are aligned with each other along the first direction D1 and spaced by an intermediate distance (d').

The intermediate distance (d') is substantially equal to the sum of the strokes performed, parallel to the first direction D1, by the units 18, 19 of the first 16 and the second transfer roller 17.

Preferably, the separating unit 25 is equipped with spacer means 62 configured for moving the first 60 and/or the second carriages 61 along a separating direction "F" parallel to the first direction D1.

More specifically, the spacer means 62 are designed for moving the carriages 60, 61 between a close axial position, wherein each first carriage 60 is aligned and positioned at the predetermined intermediate distance (d') from the respective second carriage 61, and a far axial position wherein the carriages 60, 61 are positioned at the above-mentioned operating distance (d), which is greater than the intermediate distance (d').

Thus, during the transfer of the pair of pieces 14 and 15, the spacer means 62 perform a translation of each carriage 60, 61 along respective directions opposite to each other and parallel to the first direction D1, in such a way as to space the pieces 14 and 15 of the pair up to the operating distance (d) of application on the band 22.

In other words, from the cutting of the continuous strip 9 of elastomeric material to their application in pairs on the continuous band 22 of absorbent material, the first 14 and the second 15 pieces undergo a first spacing, by the first 16 and the second 17 roller, for being transferred in pairs spaced by the intermediate distance (d'), and subsequently undergo a second spacing, by the spacer means 62, for being transferred and then applied on the continuous band 22 mutually spaced by the distance (d).

It should be noted that the spacer means 62 might be active only on the first carriages 60 or only on the second carriages 61.

However, preferably, the spacer means 62 are associated with both the first 60 and the second carriages 61 and are configured to move them simultaneously towards and away from each other between the close axial position and the far axial position.

It should be noted that the term "axial" is used to denote a movement parallel, or mainly aligned, with the first axis D1.

On the contrary, when the term "circumferential" acceleration is used in this text, it refers to a feed direction around the axis of rotation of a roller or of a rotatable drum about an axis parallel to the first direction D1.

Preferably, the spacer means 62 comprise a plurality of linear actuators 63 each associated with a respective first carriage 60.

Advantageously, in this way the relative movement between the first 60 and the second carriages 61 is independent of the movement of the other units of the device 1, which makes possible any adjustment of the operating distance without the need for modifications to the kinematic mechanisms.

It should be noted that, preferably, the spacer means 62 comprise a further plurality of linear actuators 64 each associated with a respective second carriage 61.

Alternatively, there might be a mechanical transmission for transmitting the drive from a single linear actuator 63 both to a first carriage 60 and to the corresponding second carriage 61.

In the embodiment illustrated, each linear actuator 63 associated with a first carriage 60 is opposite a linear actuator 64 associated with the respective second carriage 61.

The linear actuators 63, 64 are preferably aligned along the line of separation "F".

In the preferred embodiment, each linear actuator 63, 64 is defined by a linear electric motor.

In this regard, the device comprises a control unit (not illustrated) associated with the linear actuators 63, 64 for controlling the movement.

Advantageously, it is therefore very easy for the operator to vary the operating distance (d) by means of a user interface associated with the control unit, thus avoiding long setup times or structural changes to the kinematic mechanisms.

Each linear actuator 63, 64 comprises a movable part 63a, 64a and a fixed part 63b, 64b.

Preferably, the fixed part 63b, 64b is defined by a wired guide 65, connected to the control unit and forming the motor of the linear actuator 63, 64. The guide 65 extends along the direction of separation "F".

On the contrary, the mobile part 63b, 64b is defined by a magnet which is slidable along the guide 65 on which the carriage 60, 61 is anchored.

Thus, the fixed part 63a, 64a of the linear actuator 63, 63 is defined by an electromagnet or electromagnetic system which is excitable by the passage of current, whilst the mobile part 63b, 64b is defined by one or more magnets (permanent), which do not require any wiring.

Advantageously, in this way the masses translated, that is to say, in movement, are considerably reduced and the stresses induced by the inertias involved are minimised.

Moreover, since the power supply and control wires of the actuators are associated with the fixed part 63a, 64a, they are less stressed and hence less subject to wear and breakage, with obvious advantages in terms of reliability of the system.

Preferably, the spacer means 62 comprise a core 62a rotatable about an axis parallel to the first direction D1 and rotation means 62b operatively associated with the rotatable core 62a.

The linear actuators 63, 64 are radially anchored to the core.

More specifically, each guide 65 is oriented parallel to the first direction D1 and protrudes radially from the core 62a. It should be noted that the guides 65 are preferably spaced at equal angles to each other about the axis of rotation of the core 62a.

Each guide 65 and, more specifically, the first 60 and the second carriage 61 associated with it, are substantially tangential to the first 16 and the second transfer roller 17, respectively, at the third S3 and fourth S4 release station.

It should be noted that, in order to keep the pieces 14, 15 adhered to the first 60 and second carriage 61, the separating unit 25 comprises means 66 for generating a vacuum placed in fluid communication with each first 60 and second carriage 61.

In this regard, it should be noted that the carriages 60, 61 are equipped with at least one operating suction surface 60a, 61a associated with the means for generating the vacuum 66.

Preferably, the means for generating a vacuum are placed in fluid communication with the operating surface 60a, 61a of the carriages through a conduit (not illustrated) extending inside the guides 65.

More specifically, each guide 65 has at least one oblong opening 71 defining an end section of a respective conduit.

Each carriage 60, 61 is equipped with a sealing tab 72 abutted to the guide 65 and superposed, in each position of the carriage 60, 61, on the oblong opening 71.

The oblong opening 71 and the sealing tab 72 have a same main direction of extension, corresponding to the direction of sliding of the carriages 61, 61.

More specifically, the sealing tab 72 is slidably superposed on the oblong opening 71 and has an extension, along the main direction of extension, greater than the oblong opening 71.

In other words, in each operating position of the carriage 60, 61, the sealing tab 72 is superposed on the oblong opening 71, occluding the conduit and allowing the generation of the vacuum at the operating surface 60a, 61a.

Advantageously, in this way, the means for generating the vacuum 66 are kept operative in all the positions of the carriages 60, 61 without the need for preparing cables or movable/flexible conduits, which are often the subject of faults.

The application unit 20 also comprises an acceleration station 27 located operatively downstream of the separating unit 25 designed to receive the first 14 and the second piece 15 positioned at the operating distance (d).

The acceleration station 27 is configured so as to accelerate the feed speed of the first 14 and the second piece 15 in such a way that it is equivalent to a feed speed of the continuous band 22 of absorbent material in the machine.

Preferably, the acceleration station 27 comprises at least one rotary unit 67 equipped with at least one seat 68 for receiving a pair of pieces 14, 15 positioned at the operating distance (d) and having weight and dimensions less than that of the separating unit 25.

Advantageously, this allows the separation of the pieces at a reduced speed, performing the acceleration of the pieces by means of a unit which is less critical from the point of view of the inertias.

The acceleration station 27 is also equipped with movement means 70 associated with the rotary unit 67 and configured for imparting to it an angular speed variable between a minimum value, wherein the seat 68 has a feed speed equal to a peripheral speed of the spacer means 62, and a maximum value, wherein the seat 68 has a feed speed equal to a feed speed of the continuous band 22 of absorbent material.

Thus, the separating unit 25 has a peripheral speed "vrd" of feeding the respective carriages 60, 61 and the rotary unit 67 of the acceleration station 27 is able to pick up at the fifth station S5 the pairs of pieces 14 and 15 with a feeding speed of the relative seat 68 equal to the speed "vrd".

Moreover, the rotary unit 67 is able to impart an acceleration to the relative seat 68 and, therefore, to the corresponding pair of pieces 14 and 15 picked up, for transferring and coupling the pair of pieces 14 and 15 to the continuous band 22 of absorbent material with a speed equal to a speed "vc" of feeding the band 22.

Preferably, the variation of the angular speed of the rotary unit 67 is performed by the action of actuating means, more preferably of the cam type (not shown).

Structurally, the rotary unit 67 comprises a central core 67a and at least one pair of radial arms 69, each extending away from the central core 67a up to an end portion 69a designed to receive the pieces 14, 15. It should be noted that the radial arms could also be more than two.

The end portion 69a of each arm radial 69 is tangential to the carriages 60, 61 of the separating unit 25 at a sixth station S6, for applying the pairs of pieces 14 and 15.

To allow this pick up, suction means are associated at the end designed to generate a negative pressure at the end portion 69a.

Similarly, the above-mentioned conveyor roller 11 transports the continuous and alternating succession 13 of first 14 and second 15 pieces with a feeding speed "vrc", and the first 16 and the second 17 transfer rollers, tangent to the conveyor roller 11 at, respectively, the first S1 and the second S2 pick-up stations, are also able to vary the feeding speed of the respective units 18 and 19 for picking up the pieces 14 and 15 with a speed equal to the above-mentioned speed "vrc" and then release the pieces 14 and 15 to the separating unit 25 with a speed equal to the above-mentioned speed "vrd".

Each of the transfer rollers 16 and 17 comprises a plurality of concentric units 28a, 28b, 28c rotating about a shared axis of rotation, parallel to the first direction D1.

More in detail, according to the preferred embodiment, the roller comprises a first inner unit 28a, a second intermediate unit 28b and a third outer unit 28c.

The axis of rotation of the units 28a, 28b, 28c coincides with the axis B of rotation of the transfer roller 16, and it is defined by a shaft 29 fixed and integral with a frame of the machine 1.

For simplicity of description, the description below refers only to the first transfer roller 16, since, as stated above, it is preferable that the first 16 and the second 17 transfer rollers are equal to each other.

It should be noted that the description for the first roller 16 is to be considered absolutely valid and the same, with regard to the references to components and drawings, for the second roller 17, too.

Figure 6:
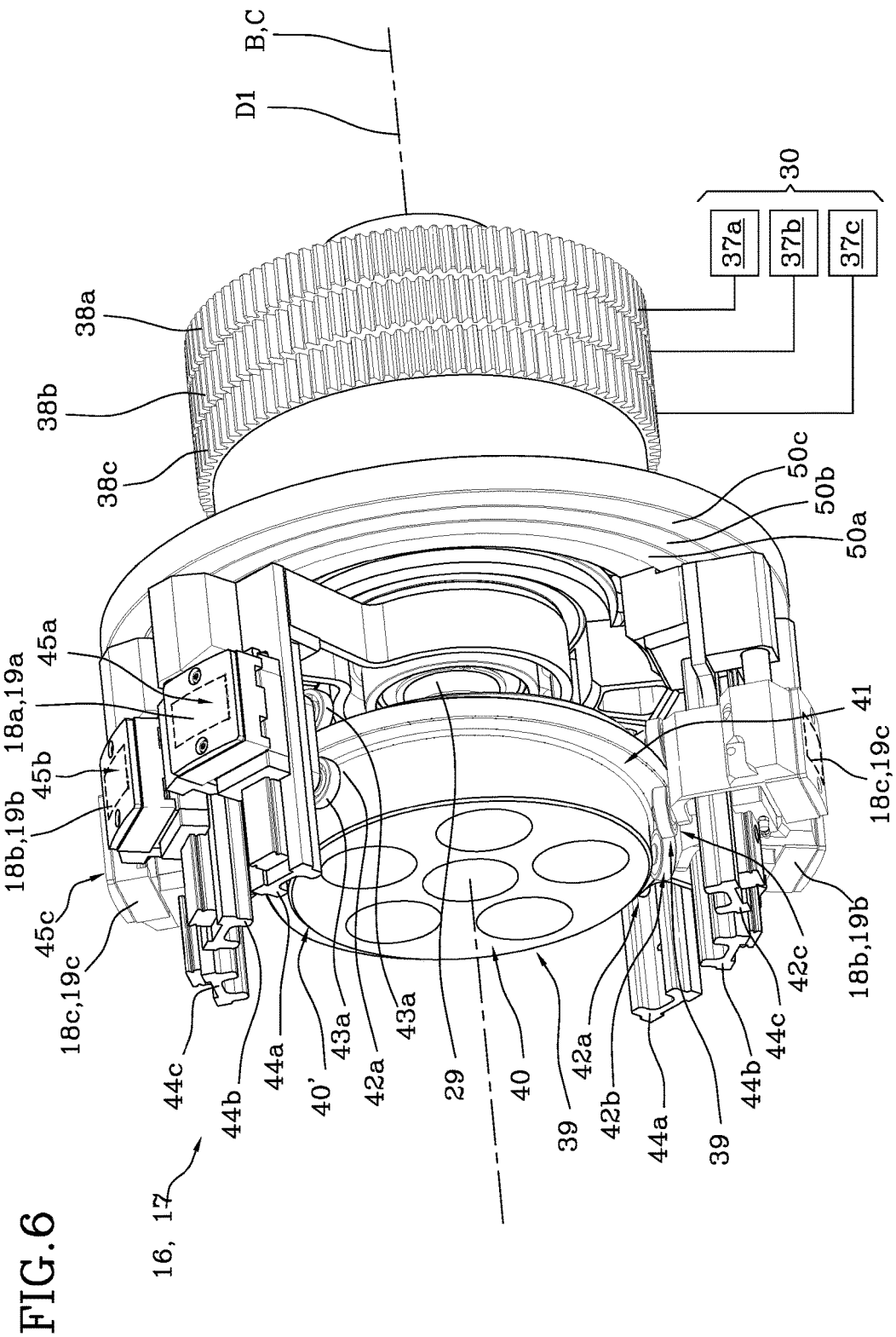
FIG. 6 is a perspective view of a third detail of the device of FIG. 1.
Figure 12:
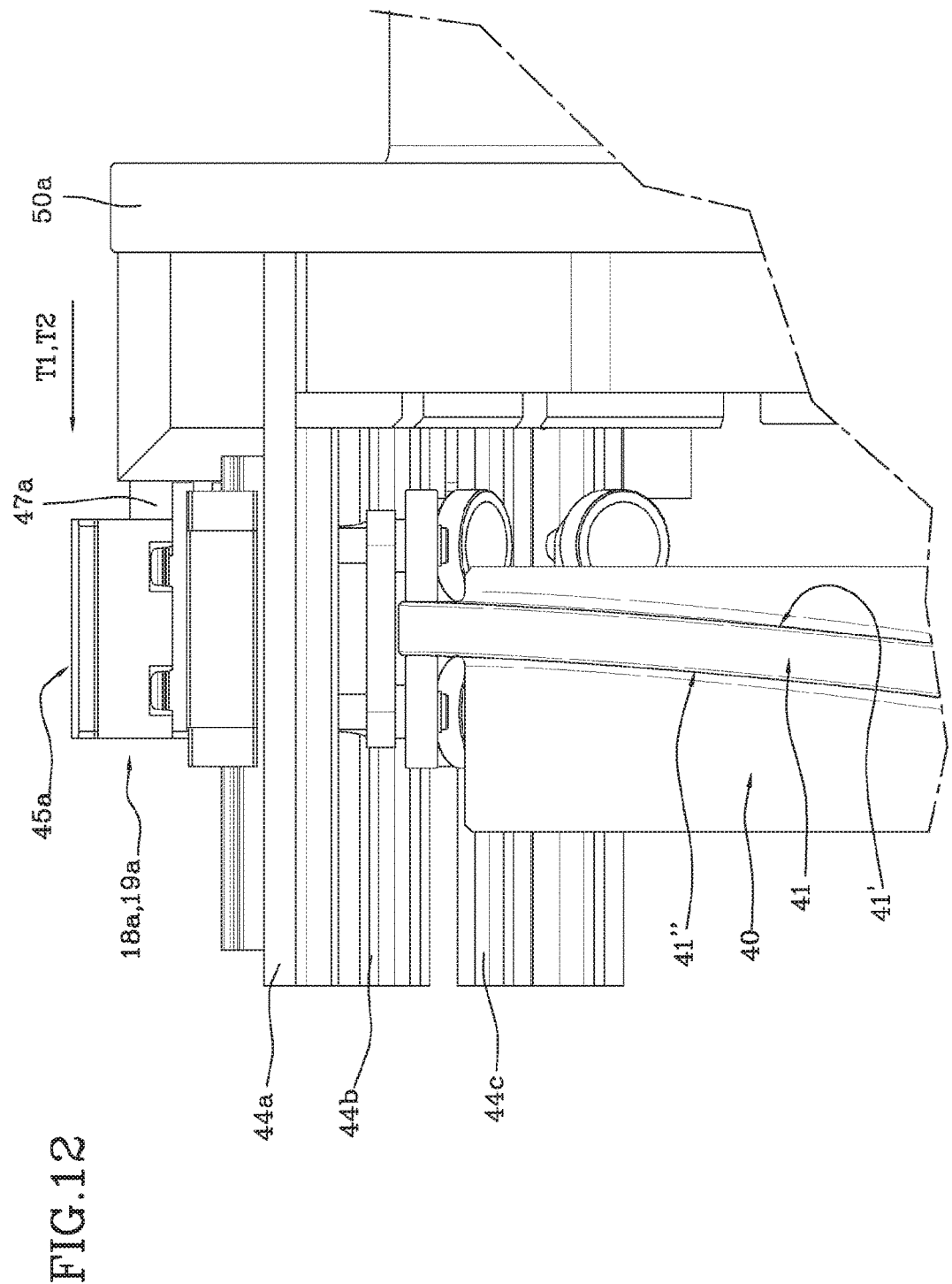
FIGS. 12 and 13 are enlarged side views of the fourth detail of FIG. 11, according to respective operating configurations.
Figure 13:
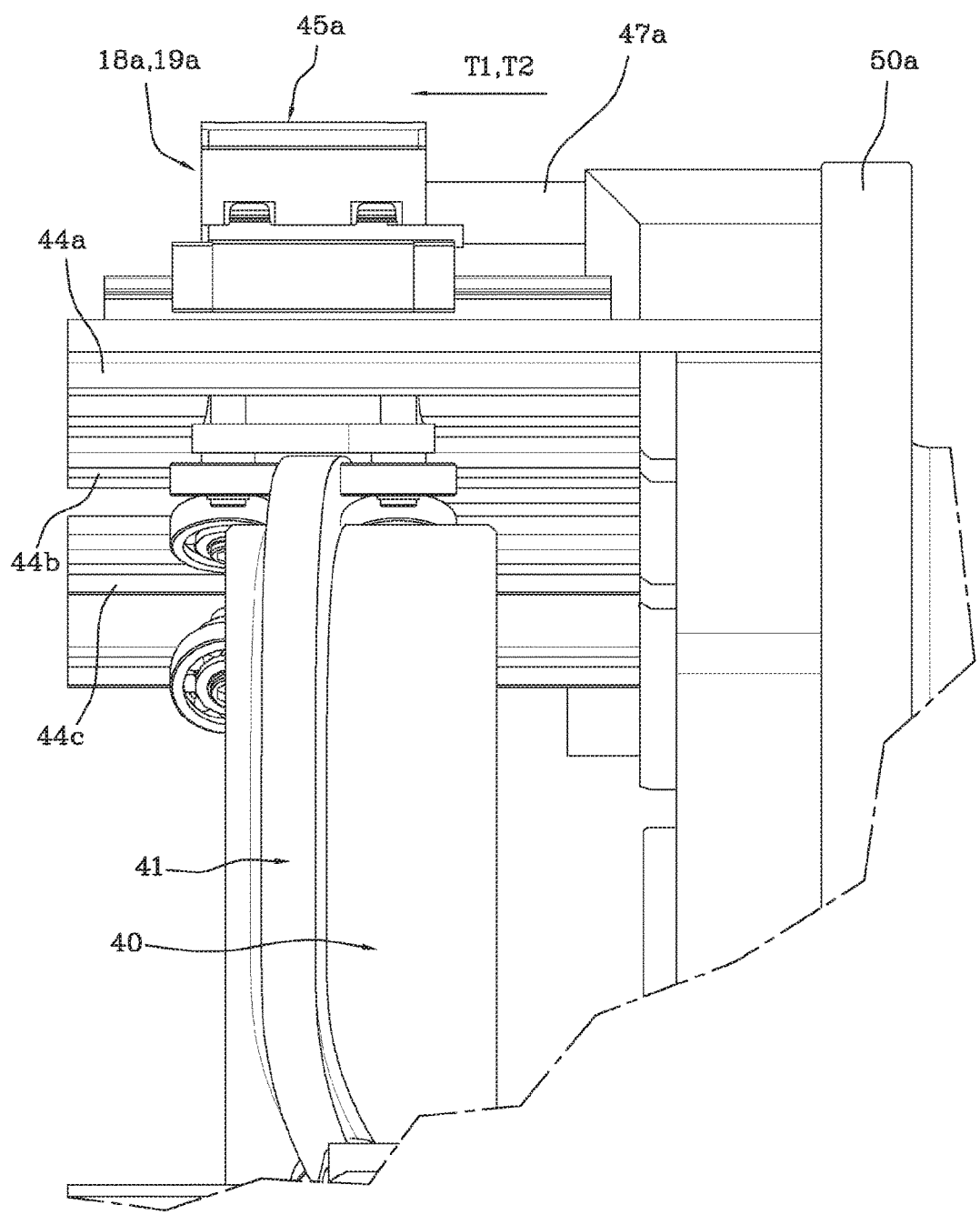

Looking in more detail, as shown in FIG. 6, each of the units 28a, 28b, 28c carries at least one respective unit 18a, 18b, 18c of the transfer roller 16. In the specific case of the preferred and illustrated embodiment, each unit 28a, 28b, 28c carries a respective pair of units 18a, 18b, 18c, positioned symmetrically opposite each other relative to the axis B of rotation of the unit 28a, 28b, 28c.

The transfer roller 16 comprises motor means, labelled 30 in FIG. 8, which drive each of the units 28a, 28b, 28c and define for each of them a respective law of motion, for picking up the first pieces 14 from the conveyor roller 11 with a first speed, equal to the speed "vrc" of feeding the continuous and alternating succession 13 drawn by the conveyor roller 11, and for releasing the first pieces 14 to the separating unit 25 with a second speed, equal to the speed "vrd" of feeding the units 60, 61 of the separating unit 25.

More specifically, the units 28a, 28b, 28c are movable, independently of each other and the respective laws of motion defined by the motor means 30 are, therefore, also independent of each other.

For further simplicity of description, the references to identical and corresponding components for each unit will be indicated with the same numbering and those associated with the first inner unit 28a will be indicated with "a", those associated with the second intermediate unit 28b will be indicated with "b" and those associated with the third outer unit 28c will be indicated with "c".

As shown more clearly in FIG. 8, the units 28a, 28b, 28c are able to move independently of each other thanks to respective pairs 31a, 31b, 31c of concentric bearings with gradually increasing dimensions.

More in detail, a first pair 31a of bearings is fitted on the fixed shaft 29 and carries the first unit 28a. A second pair 31b of bearings, with a diameter greater than the first pair, is fitted on the first unit 28a and carries the second unit 28b. Lastly, a third pair 31c of bearings, with a diameter greater than the first pair and the second pair, is fitted on the second unit 28b and carries the third unit 28c.

Each unit 28a, 28b, 28c comprises a respective main body 32a, 32b, 32c, which is substantially tubular in shape. Each main body 32a, 32b, 32c has, respectively, a relative inner surface 33a, 33b, 33c and a relative outer surface 34a, 34b, 34c.

The first pair 31a of bearings is, therefore, mounted between the shaft 29 and the inner surface 33a of the first unit 28a; the second pair 31b is mounted between the outer surface 34a of the first unit 28a and the inner surface 33b of the second unit 28b; the third pair 31c is mounted between the outer surface 34b of the second unit 28b and the inner surface 33c of the third unit 28c.

Moreover, each unit 28a, 28b, 28c has, respectively, a front portion 35a, 35b, 35c and a rear portion 36a, 36b, 36c.

At the rear portion 35a, 35b, 35c each unit 28a, 28b, 28c is connected, separately from the others, to the above-mentioned motor means 30.

In detail, the motor means 30 comprise a plurality of motor units, schematically represented by the blocks 37a, 37b, 37c (FIG. 6). The motor units 37a, 37b, 37c are separate and distinct from each other and each of them is connected to a respective unit 28a, 28b, 28c. More in detail, a first motor unit 37a is connected to the first unit 28a, a second motor unit 37b is connected to the second unit 28b and a third motor unit 37c is connected to the third unit 28c.

Each of the motor units 37a, 37b, 37c is able to define the law of motion for the unit to which it is connected comprising a non-circular gear wheel gearing (not illustrated), or by using three different electronic cams (also not illustrated) consisting of three different motors, each coupled to the respective motor unit.

Each of the gearings is connected to the respective unit 28a, 28b, 28c by means of a plurality of gear wheels 38a, 38b, 38c integral with the units 28a, 28b, 28c at the rear portion 35a, 35b, 35c of the units (FIGS. 4 and 6).

According to the preferred embodiment, the transfer roller 16 has a first 38a, a second 38b and a third 38c gear wheel, integral, respectively, with the first 28a, the second 28b and the third 28c unit.

The gear wheels 38a, 38b, 38c also have equal diameters and are substantially adjacent to each other along the axis B of rotation of the roller 16.

The first transfer roller 16 comprises means 39 for translating the relative units 18a, 18b, 18c along a first direction T1 parallel to the first direction D1 (FIGS. 10 and 11), between a position for picking up the first pieces 14 from the conveyor roller 11, at the first station S1, and a position for releasing the pieces 14 to the separating unit 25, at the third station S3.

As shown in FIG. 6, the means 39 for translating the units 18a, 18b, 18c comprise a fixed cam 40 having a relative profile 41, the cam 40 being integral with the above-mentioned shaft 29 of the roller 16. The translational means 39 also comprise a plurality of carriages 42a, 42b, 42c, slidably coupled with the profile 41 of the cam 40, each of which is mounted on a respective unit 18a, 18b, 18c of the roller 16.

More in detail, in the example illustrated, the cam 40 is of the cylindrical type and the profile 41 is defined by a projection made on a cylindrical lateral surface 40' of the cam 40.

Each carriage 42a, 42b, 42c comprises a pair of rollers 43a, 43b, 43c slidably coupled on respective opposite surfaces, labelled 41' and 41", of the profile 41 of the cam 40.

The transfer roller 16 comprises, for each relative unit 18a, 18b, 18c, a guide 44a, 44b, 44c, connected to the respective unit 28a, 28b, 28c and integral with it in rotation. Each guide 44a, 44b, 44c has a main direction of extension along a direction parallel to the first reference direction D1.

During the rotation of the units 28a, 28b, 28c about the axis B of rotation, each carriage 42a, 42b, 42c follows the profile 41 of the cam 40 and, consequently, the unit 18a, 18b, 18c translates on the respective guide 44a, 44b, 44c between the pick up position of the first pieces 14 from the conveyor roller 11, wherein the respective unit 18a, 18b, 18c is in a position close to the relative unit 28a, 28b, 28c, and the release position of the pieces 14 to the separating unit 25, wherein the unit 18a, 18b, 18c is in a position far from the relative unit 28a, 28b, 28c.

During the movement from the pick up position to the release position, each unit 18a, 18b, 18c translates, along the above-mentioned direction T1, the respective first piece 14 picked up from the continuous succession 13, by a distance equal to half the above-mentioned intermediate distance.

Similarly, the second transfer roller 17 translates the second pieces 15 by a distance equal to half the intermediate distance, along a second direction T2 parallel to the direction D1 and opposite in direction to the direction T1.

In this way, when the first 14 and the second 15 pieces are released to the separating unit 25 to form the above-mentioned pairs, the distance between them is equal to the distance d'.

Each unit 18a, 18b, 18c has a respective suction face 45a, 45b, 45c for retaining the piece 14. The suction is obtained using the holes 46a, 46b, 46c each respective face 45a, 45b, 45c is equipped with.

The holes 46a, 46b, 46c of each face 45a, 45b, 45c are connected to a respective hollow rod 47a, 47b, 47c, which in turn is in fluid communication with a suction source, indicated schematically by the block 48.

Label 47a in FIG. 10 denotes the stem of the unit 18a connected to the first inner unit 28a. The stem 47a is slidable inside a seat 49a also connected to the suction source 48. Moreover, the seat 49a has a length such that the stem 47a always remains engaged with the seat 49a during the sliding of the unit 18a, even in the condition of maximum excursion of the unit 18a, at the release position of the piece 14.

This guarantees that the piece 14 remains correctly gripped until the moment of its release to the unit 25.

Obviously, what has just been described is to be considered similarly valid for the units 18b and 18c.

The first transfer roller 16 also comprises a plurality of concentric elements 50a, 50b, 50c, each of which is connected to a respective unit 18a, 18b, 18c and is integral with it in rotation. More in detail, the elements 50a, 50b, 50c are substantially annular in shape.

The annular elements 50a, 50b, 50c constitute valve elements for the respective units 18a, 18b, 18c, since they define, during the rotation of the units 18a, 18b, 18c about the axis B of rotation, a first operating condition, wherein the suction holes 46a, 46b, 46c are placed in fluid communication with the suction source 48 for retaining the first pieces 14, and a second operating condition, wherein the fluid communication between the holes 46a, 46b, 46c and the suction source 48 is interrupted for releasing the pieces 14.

Preferably, the first roller 16 comprises a first 50a, a second 50b and a third 50c annular element connected, respectively, to the first 18a, the second 18b and the third 18c unit.

Preferably, the annular elements 50a, 50b, 50c are made from self-lubricating material, for example Teflon, in such a way as to prevent the formation of friction, between two adjacent elements, during the rotation of the units 18a, 18b, 18c.

The fluid communication between the holes 46a, 46b, 46c and the suction source 48 is achieved, for each unit 18a, 18b, 18c, by means of a respective through hole 51a, 51b, 51c, made on the respective annular element 50a, 50b, 50c, the hole 51a, 51b, 51c placing in communication the source 48 with the respective seat 49a, 49b, 49c of each unit 18a, 18b, 18c.

Since, according to the preferred embodiment, each unit 28a, 28b, 28c carries a pair of units 18a, 18b, 18c diametrically opposite the axis B of rotation of the first roller 16, each annular element 50a, 50b, 50c has a pair of holes 51a, 51b, 51c, also diametrically opposite the axis B, each of which places the source 48 in fluid communication with a respective unit 18a, 18b, 18c of the pair.

Since each annular element 50a, 50b, 50c is integral with the respective unit 18a, 18b, 18c, the above-mentioned hole 51a, 51b, 51c always places in communication each seat 49a, 49b, 49c of the units 18a, 18b, 18c and the respective suction holes 46a, 46b, 46c with the suction source 48.

The first roller 14 is equipped with a further element, not illustrated, which also acts as a valve and it is interposed between the annular elements 50a, 50b, 50c and the suction source 48 and allows definition of the fluid connection steps with the suction source 48 and interruption of the connection.

Looking in more detail at the operation of the machine 1, it receives the continuous band 22 of absorbent material, which is transported by the conveyor 21 along the second direction D2.

The machine 1 also receives the strip 9 of elastomeric material which is fed from the feeding unit 10 to the conveyor roller 11.

The strip 9 is cut at the conveyor roller 11, by the cutting roller 23, into the above-mentioned continuous and alternating succession 13 of first 14 and second 15 pieces, constituting, as already stated, the first and second flaps of the absorbent article 2.

The continuous strip 9 and the succession 13 of pieces 14 and 15 are moved by the feeding unit 10 and by the conveyor roller 11 following a first stretch P1 of the overall path of the pieces 14 and 15 from the cutting of the strip 9 to their application on the band 22 made of absorbent material.

At the first station S1 the first transfer roller 16 picks up from the conveyor roller 11 the first pieces 14 and feeds them to the separating unit 25 following a second stretch P2 of path.

The second roller 17 picks up, at the second station S2, the second pieces 15 and feeds them to the separating unit 25 following a third stretch P3 of path, different from the second stretch P2.

The first 16 and the second 17 rollers pick up the respective pieces 14 and 15 varying the feeding speed of the relative respective units 18 and 19 until it is changed to the value of the above-mentioned peripheral speed "vrc" of the conveyor roller 11.

After picking up the respective pieces 14 and 15, each roller 16 and 17 holds the relative pieces 14 and 15, varying again the speed of the relative units 18 and 19 to change it to the value of the speed "vrd" of the carriages 60, 61 of the separating unit 25.

The transfer rollers 16 and 17 then translate the relative pieces 14 and 15 transported along the respective directions T1 and T2 parallel to the first direction D1 and, since these directions T1 and T2 have directions opposite to each other, the separating unit 25 receives an above-mentioned pair of first 14 and second 15 pieces, which are mutually aligned and spaced along the first reference direction D1 by the intermediate distance (d').

As stated above, the first 16 and the second 17 transfer rollers rotate in an anticlockwise direction, whilst the separating unit 25 rotates in a clockwise direction, so, the second roller 17 releases firstly the relative second piece 15, at the fourth station S4, then the first roller 16 releases the relative first piece 14 at the third station S3.

Therefore, the separating unit 25 forms the respective pairs of pieces 14 and 15 at the third station S3, when it receives the first piece 14.

At the third station S3 there is the joining of the second P2 and the third P3 stretch into a single fourth stretch, labelled P4 in FIG. 1, which each pair of pieces 14 and 15 travels along from the third station S3 to the fifth station S5, in the direction of the acceleration station 27.

The separating unit 25 then transfers the pairs of pieces 14 and 15, the acceleration station 27 following the fourth stretch P4 of shared path During the feeding along the fourth stretch P4, the separating unit 25 forms the further mutual spacing of the pieces 14 and 15 of each pair, until moving them to a distance equal to the distance (d) of application of the pair on the continuous band 22 of absorbent material.

FIGS. 3a, 3b and 3c schematically indicate the sequence of steps performed by the machine 1 for making the pairs of pieces 14 and 15, or lateral flaps, to be applied to the continuous band 22.

Initially, transversal notches are made on the continuous strip 9 of elastomeric material to define the continuous and alternating succession 13 of first 14 and second 15 pieces (FIG. 3a). This step is implemented by notching, using the cutting roller 23, the strip 9 with respective slanting notches which define first 14 and second 15 trapezoidal pieces.

The first 14 and the second 15 pieces are then picked up, respectively, by the first 16 and the second 17 transfer rollers and translated along the respective directions T1 and T2, until they are spaced by the intermediate distance (d') (FIG. 3b).

More in detail, as stated, the pieces 14 and 15 are substantially trapezoidal in shape and the first 16 and the second 17 transfer rollers translate the respective pieces along the directions T1 and T2, mutually away from the longitudinal axis L of the strip 9, keeping the longer side facing towards the axis L and moving them both to a distance from the axis L equal to half the above-mentioned intermediate distance d'.

Lastly, the separating unit 25 performs the further spacing of the pieces 14 and 15 of the pair, carrying them to a mutual distance equal to the operating distance (d) of transfer to the acceleration station 27 and application on the band 22.

At the fifth station S5, the acceleration station 27 picks up the pairs of pieces 14, 15 with a speed of feeding the relative suction seats 52 equal to the value of speed "vrd" of the carriages 60, 61 of the separating unit 25 and transfers the pairs of pieces 14 and 15 following a fifth stretch P5 of path, increasing their feeding speed for applying them on the band 22 of absorbent material with a speed equal to the speed "vc" of feeding the band 22.

When the pairs of pieces 14 and 15 have then been applied to the band 22 of absorbent material the absorbent articles 2 joined together move forward towards the cutting unit 23 and the outfeed of the machine, following with speed "vc" a sixth stretch S6 of path, substantially defined by the conveyor 21.

With regard to the operation of each transfer roller, a more detailed description of the movement and the mutual coordination of the relative components is given below, with particular reference to the movement and coordination of the units 18 carried by each unit 28a, 28b, 28c.

In order to make the description of the units 18 of each pair associated with the respective unit 28a, 28b, 28c of the roller 16 clearer, 18a' and 18a' will indicate the units of the first pair carried by the first unit 28a, 18b' and 18b" will indicate the units of the pair carried by the second unit 28b and 18c' and 18c" will indicate the units of the pair carried by the third unit 28c, respectively.

During the rotation about the axis B, the speed of feeding the unit 18a' of the first unit 28a is changed to the value of the peripheral speed "vrc" of the conveyor roller 11, for picking up the first piece 14 at the first station S1.

It is preferable that the unit 18a' reaches that speed before arriving at the first station S1 and it is also preferable that it maintains it for a predetermined stretch downstream of the first station S1, so as to guarantee the correct pick up of the piece 14.

After the pick up, the speed of the unit 18a' is changed to the value of the peripheral speed "vrd" of the separating unit 25.

More specifically, according to the preferred embodiment, the spacer has a peripheral speed "vrd" greater than the peripheral speed "vrc" of the conveyor roller 11, so, after picking up the first piece 14, the unit 18a' is accelerated when moving from the first S1 to the third S3 station.

It is also preferable that the unit 18a' reaches the speed "vrd" before arriving at the third station S3 and that it maintains it for a predetermined stretch downstream of the station, so as to guarantee the correct release of the first piece 14 to the separating unit 25.

After releasing the first piece 14, in reaching again the first station S1, the unit 18a' is slowed down and its speed is returned to the value of the peripheral speed "vrc" for picking up a new first piece 14 from the conveyor roller 11.

As already indicated, each unit 28a, 28b, 28c carries a pair of units 18a' and 18a", the one diametrically opposite the other relative to the axis B of rotation.

For this reason, each unit 18a' and 18a" is given the same acceleration and the same deceleration given to the other.

In other words, when the speed of the unit 18a' is slowed down to the speed "vrc" for picking up from the conveyor roller 11 the first piece 14, the unit 18a" undergoes the same slowing down.

More in detail, during the step for picking up the first piece 14 by the unit 18a', the unit 18a" is empty as it has just released the relative first piece 14 to the separating unit 25 and is therefore moving from the third S3 to the first S1 station.

When, then, the unit 18a', carrying the first piece 14, is accelerated to change its feeding speed to the peripheral speed "vrd" of the separating unit 25, the unit 18a" simultaneously accelerates.

When the unit 18a" then approaches the first station S1, it is slowed down to the speed "vrc", and at the same time the unit 18a', which has just transferred to the separating unit 25 the relative first piece 14, is also changed to the speed "vrc".

The unit 18a", which has picked up from the conveyor roller 11a first piece 14, is now accelerated until reaching the speed "vrd" and simultaneously the unit 18a' is also accelerated.

Lastly, after the unit 18a" has released the piece 14 to the spacer roller 11, the unit 18a' is slowed down to pick up a new piece 14 from the conveyor roller 11 and restart the cycle.

Obviously, according to the above description, the unit 18a" also reaches the speeds "vrc" and "vrd" before reaching the first S1 and the third S3 station, and they are maintained for a predetermined stretch downstream of the stations, so as to guarantee the correct pick up and the correct release of the first piece 14 also by the unit 18a".

To have the correct coordination of the steps for picking up and releasing the first piece 14 by the unit 18a' and the unit 18a" according to the above-mentioned predetermined speeds, it is preferable that the first S1 and the third S3 stations are positioned, along the path traveled by the units during their rotation about the axis B, spaced from each other by an arc-shaped stretch of the above-mentioned path having a subtended angle, labelled a in FIG. 1, substantially equal to 90°.

The spacing between the first S1 and the third S3 stations allows maximum continuity between the steps for picking up and releasing the first pieces 14 without interferences between the movements of the various units 18a, 18b, 18c during the respective accelerations and decelerations.

Further, with regard to the units 18b', 18b" and 18c', 18c" carried by the other units 28b and 28c, they are given the same accelerations and the same decelerations as the units 18a', 18a" carried by the first unit 28a described above.

Further, the conveyor roller 11 and the separating unit 25 rotate with constant rotational speed, so, to have continuous pick up and release of the pieces 14 by the first transfer roller 16, it is preferable that each unit 18a', 18a", 18b', 18b", 18c', 18c" of the respective unit 28a, 28b, 28c is accelerated and decelerated at the same positions whilst reaching the first S1 and the third S3 station.

The invention claimed is:

1. A device for forming and applying at least one pair of accessory elements to a continuous band of absorbent material, comprising:
    a feeding unit for feeding a continuous strip to a conveyor roller, rotating about an axis transversal to a first direction,
    a cutting unit for cutting the strip in a continuous and alternating succession of first and second pieces, comprising, respectively, first and second accessory elements of the absorbent article,
    a first transfer roller and a second transfer roller rotating about respective axes parallel to the first direction and each equipped with a plurality of picking units for picking up, respectively, the first and the second pieces, from the succession at a picking up position and their release at a release position, wherein each of the first transfer roller and the second transfer roller comprises:
    a movement device for moving the plurality of picking units, the movement device acting along a circumferential direction around the respective axis and configured for imparting to each of the plurality of picking units a respective motion between the picking up position for picking up the first and second pieces, located at the conveyor roller, and the position for releasing the first and second pieces;
    a translating device for translating the plurality of picking units, the translating device acting along a direction parallel to the first direction and configured for moving each of the plurality of picking units between a first axial position, adopted in the picking up position, and a second axial position, adopted in the release position;
    an application unit for applying the first and second pieces to the band of absorbent material including a separating unit configured for picking up one of the first pieces and one of the second pieces from the release position of the first transfer roller and the second transfer roller by respective first and second carriages; the separating unit including a spacer device suitable for moving at least one chosen from the first carriage and the second carriage along a separating direction parallel to the first direction between a close axial position, wherein each first carriage is aligned and located at a predetermined intermediate distance from a respective second carriage, and a far axial position wherein the carriages are located at an operating distance which is greater than the intermediate distance;
    wherein the spacer device comprises:
        a plurality of linear actuators each associated with the first carriage;
        a further plurality of linear actuators each associated with the second carriage, wherein each of the plurality of linear actuators is opposite to and aligned with one of the further plurality of linear actuators.

2. The device according to claim 1, wherein each linear actuator includes a linear electric motor.

3. The device according to claim 2, wherein each linear actuator comprises a movable part and a fixed part, wherein the fixed part is defined by a wired guide, connected to a control unit and forming a motor of the linear actuator and the movable part is defined by a magnet slidable along the guide on which the carriage is anchored.

4. The device according to claim 1, wherein the spacer device comprises a rotatable core on which the linear actuators are radially anchored and a rotation device operatively associated with the core.

5. The device according to claim 4, wherein each linear actuator comprises a linear guide, oriented parallel to the separating direction and protruding radially from the rotatable core, on which at least one chosen from the first carriage and the second carriage is slidable.

6. The device according to claim 5, and further comprising a vacuum device for generating a vacuum positioned in fluid communication with each of the first and second carriages; the first and second carriages including at least one operating suction surface associated with the vacuum device.

7. The device according to claim 6, wherein the vacuum device comprises a plurality of conduits extending inside the guides of the carriages, each having an end section defined by an oblong opening made in the guide; the carriages each being equipped with a sealing tab slidably superposed on the oblong opening and shaped in such a way as to occlude the oblong opening in both the close and far axial positions of the respective carriage.

8. The device according to claim 1, wherein the application unit further comprises an acceleration station operatively located downstream of the separating unit so as to receive the first and second piece positioned at the operating distance and configured to accelerate the feeding speed of the first and second piece in such a way as to be equivalent to a feeding speed of the continuous band of absorbent material.

9. The device according to claim 8, wherein the acceleration station comprises at least one rotary unit including at least one seat for receiving the first and second pieces positioned at the operating distance and having a weight and dimensions less than that of the separating unit; the acceleration station also including a further movement device associated with the at least one rotary unit and configured for imparting to the at least one rotary unit a speed of rotation variable between a minimum value, wherein the at least one seat has a feed speed equal to a peripheral speed of the spacer device, and a maximum value, wherein the feeding speed of the at least one seat is equal to the feeding speed of the continuous band of absorbent material.

10. The device according to claim 9, wherein the at least one rotary unit comprises a central core and at least one pair of radial arms, each extending away from the central core up to an end portion suitable for receiving the first and second pieces.

11. The device according to claim 1, wherein the movement device for moving the plurality of picking units comprises a plurality of concentric units rotating independently of each other about a shared axis of rotation, each of the plurality of concentric units carrying at least one respective unit of the plurality of picking units and at least one motor for defining a respective motion for each of the plurality of concentric units.

12. A machine for making absorbent sanitary article, comprising:
- the device for forming and applying the at least one pair of accessory elements on the continuous band of absorbent material according to claim 1;
- a conveyor for feeding the continuous band of absorbent material along a second direction, at right angles to the first direction, facing the application unit of the device;
- a further cutting unit for cutting the continuous band into pieces of absorbent material suitable for constituting single absorbent articles, following application of the accessory elements by the device for forming and applying the at least one pair of accessory elements on the continuous band of absorbent material.

* * * * *